United States Patent
Auner et al.

[11] Patent Number: 6,153,781
[45] Date of Patent: Nov. 28, 2000

[54] SILACYCLOBUTENE COMPOUNDS, METHODS OF PREPARING SAME, AND POLYMERS FORMED THEREFROM

[75] Inventors: Norbert Auner, Raum; Martin Grasmann, Berlin, both of Germany

[73] Assignee: Dow Corning, Ltd., Barry, United Kingdom

[21] Appl. No.: 09/298,818

[22] Filed: Apr. 23, 1999

[51] Int. Cl.[7] .................................................. C07F 7/08
[52] U.S. Cl. ........................... 556/406; 528/32; 526/279
[58] Field of Search ................ 556/406; 528/32; 526/279

[56] References Cited

U.S. PATENT DOCUMENTS

| | | | |
|---|---|---|---|
| 3,445,495 | 5/1969 | Nelson et al. | 556/406 |
| 3,565,934 | 2/1971 | Fink | 556/406 |
| 3,687,995 | 8/1972 | Jonas et al. | 556/406 |
| 5,608,094 | 3/1997 | Lee et al. | 556/406 |
| 5,777,051 | 7/1998 | Auner et al. | 526/279 |

FOREIGN PATENT DOCUMENTS 2 326 417  12/1998  United Kingdom.

OTHER PUBLICATIONS

Angew. Chem. Int. Ed. Engl. 30 (May 1991) No. 9, Auner et al., 1151–1152.
Chem. Ber. Jun. 1993, 126, Auner et al., 2177–2186.

*Primary Examiner*—Paul F. Shaver
*Attorney, Agent, or Firm*—Larry A. Milco

[57] ABSTRACT

A silacyclobutene compound having the formula:

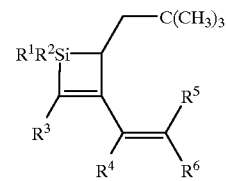

wherein $R^1$ and $R^2$ are independently chloro, triorganosiloxy, organooxy, triorganosilyl, or a monovalent hydrocarbon group; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl. Methods of preparing the silacyclobutene compounds, silane polymers containing at least one silacyclobutene unit, and siloxane polymers containing at least one silacyclobutene unit.

25 Claims, No Drawings

SILACYCLOBUTENE COMPOUNDS, METHODS OF PREPARING SAME, AND POLYMERS FORMED THEREFROM

FIELD OF THE INVENTION

The present invention relates to silacyclobutene compounds, and more particularly to silacyclobutene compounds having a vinylic group attached to the ring C-3 position. The present invention also relates to methods of preparing the silacyclobutene compounds, to silane polymers containing at least one silacyclobutene unit, and to siloxane polymers containing at least one silacyclobutene unit.

BACKGROUND OF THE INVENTION

Silacyclobutenes, methods for the preparation thereof, and polymers containing silacyclobutene units are known in the art. For example, Auner et al. disclose the synthesis of silacyclobutenes by reaction of equimolar amounts of trichlorovinylsilane and tert-butyllithium in the presence of acetylene derivatives (Angew. Chem. Int. Ed. 1991, 30, 9, 1151–1152). In this manner, the following silacyclobutenes were obtained in 50–80% yield: 1,1-dichloro-2,3-dimethyl-4-neopentyl-1-silacyclobut-2-ene; 1,1-dichloro-4-neoptenyl-2,3-bis(trimethylsilyl)-1-silacyclobut-2-ene; 1,1-dichloro-4-neopentyl-2,3-diphenyl-1-silacyclobut-2-ene; 1,1-dichloro-3-methyl-4-neopentyl-2-(trimethylsilyl)-1-silacyclobut-2-ene; 1,1-dichloro-4-neopentyl-3 -phenyl-2-(trimethylsilyl)-1-silacyclobut-2 -2-ene; and 1,1-dichloro-3-methyl-4-neopentyl-2-phenyl-1-silacyclobut-2-ene. The silacyclobutenes are reportedly thermally stable and do not decompose even on heating for several days at 200° C.

Auner et al. disclose the synthesis of silacyclobutenes by reacting chlorovinylsilanes, tert-butyllithium, and diorganoacetylenes (Organometallics 1993, 12, 10,4135–4140). In addition to the silacyclobutenes reported in the previous reference, the following compounds were obtained: 1,1-dichloro-2,3-dimethyl-4-neopentyl-4-phenyl-1-silacyclobut-2-ene; 1,1 -dichloro-4-neopentyl-4-phenyl-2,3-bis(trimethylsilyl)-1 silacyclobut-2-ene 1,1-dichloro-4-neopentyl-2,3 ,4-triphenyl-1-silacyclobut-2-ene; 1,1-dichloro-3-methyl-4-neopentyl-4-phenyl-2-(trimethylsilyl)-1-silacyclobut-2-ene; 1,1-dichloro-4-neopentyl-3,4-diphenyl-2-(trimethylsilyl)-1-silacyclobut-2-ene; 1,1-dichloro-3-methyl-4-neopentyl-2,4-diphenyl-1-silacyclobut-2-ene; 2,3-dimethyl-4-neopentyl-1,1-bis(trimethylsiloxy)-1-silacyclobut-2-ene; 4-neoptenyl-1,1-bis(trimethylsiloxy)-2,3 bis(trimethylsilyl)1-silacyclobut-2-ene; 4-neopentyl-2,3 -diphenyl-1,1-bis(trimethylsiloxy)-1-silacyclobut-2-ene; 3 -methyl-4-neopentyl-1,1-bis(trimethylsiloxy)-2-(trimethylsilyl)-1-silacyclobut-2-ene; 4-neopentyl-3 -phenyl-1,1-bis(trimethylsiloxy)-2 (trimethylsilyl)-1-silacyclobut-2-ene; and 3 -methyl-4-neopentyl-2-phenyl-1,1-bis(trimethylsiloxy)-1-silacyclobut-2-ene. The authors report that the silacyclobutenes have surprising thermal stability and can be distilled in most cases under vacuum at temperatures up to 200° C. without decomposition.

U.S. Pat. No. 5,777,051 to Auner et al. discloses monosilacyclobutene monomers, spiro-type cyclosiloxysilacyclobutene monomers, and silane polymers containing such silacyclobutene units. One type of monosilacyclobutene monomer has the formula:

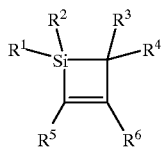

wherein $R^1$ and $R^2$ are halogen or alkoxy, $R^3$ and $R^4$ are hydrogen or alkyl having 2 to 10 carbon atoms, and $R^5$ and $R^6$ are aryl. Another type of monosilacyclobutene monomer has the formula:

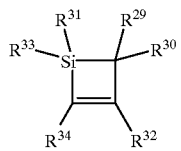

wherein $R^{29}$ and $R^{30}$ are hydrogen or alkyl having 2 to 10 carbon atoms; $R^{31}$ and $R^{33}$ are hydroxyl, alkyl, aryl, alkenyl, or alkynyl; and $R^{32}$ and $R^{34}$ are aryl. The silacyclobutene monomers and silacyclobutene polymers reportedly exhibit strong photoluminescence in the blue region of the visible spectrum when excited by ultraviolet light with a wavelength of 337 nm.

UK Patent Application GB 2326417 to Auner et al. discloses silacyclobutane compounds, silacyclobutene compounds, and siloxane polymers containing silacyclobutane and/or silacyclobutene units. The silacyclobutene compounds have the formula:

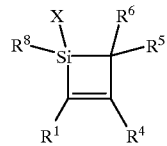

wherein $R^1$, $R^4$, and $R^5$ are independently a hydrocarbon group or hydrogen; $R^6$ is alkyl having at least 4 carbon atoms; X is a hydrolyzable group; and $R^8$ is $R^1$ or X. Examples of X include halogen and hydrocarbonoxy. The UK patent application teaches that $R^1$ and $R^4$ are preferably aromatic hydrocarbon groups. The silacyclobutene compounds are reportedly prepared by cycloaddition of a silene and an acetylene. The UK patent application also teaches that the siloxane polymers have improved resistance to low temperatures.

Although the above-cited references disclose various silacyclobutene compounds, none of the references teach the silacyclobutene compounds of the present invention having a vinylic group attached to the ring C-3 position, the methods of preparing the silacyclobutene compounds, the silane polymers, or the siloxane polymers of the present invention.

SUMMARY OF THE INVENTION

The present inventors have discovered that treating a mixture of an appropriately substituted chlorovinylsilane and a conjugated enyne with tert-butyllithium produces a silacyclobutene compound having a vinylic group attached to the ring C-3 position.

Specifically, the present invention is directed to a silacyclobutene compound having the formula:

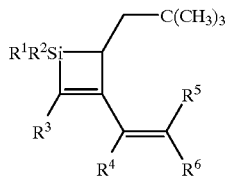

(I)

wherein $R^1$ and $R^2$ are independently chloro, triorganosiloxy, organooxy, triorganosilyl, or a monovalent hydrocarbon group; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl.

The present invention is also directed to a method of preparing a silacyclobutene compound, comprising contacting a mixture comprising a chlorovinylsilane having the formula:

$$R^1R^2ClSiCH=CH_2$$

and a conjugated enyne having the formula:

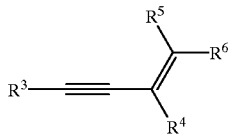

with tert-butyllithium, wherein $R^1$ and $R^2$ are independently chloro or triorganosiloxy; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl.

The present invention is further directed to a silane polymer containing at least one silacyclobutene unit having the formula:

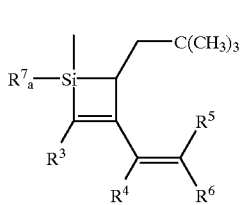

(II)

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; $R^7$ is chloro, triorganosiloxy, organooxy, triorganosilyl, or a monovalent hydrocarbon group; and a is 0 or 1; provided that $R^3$ is not aryl.

The instant invention is still further directed to a siloxane polymer containing at least one silacyclobutene unit having the formula:

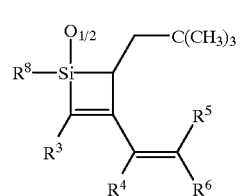

(III)

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; and $R^8$ is chloro, triorganosiloxy, organooxy, triorganosilyl, a monovalent hydrocarbon group, hydroxy, or —O—; provided that $R^3$ is not aryl.

The silacyclobutene compounds of the present invention exhibit high thermal stability. In fact, the compounds can be heated in an air atmosphere at temperatures up to 200° C. without any decomposition. Additionally, the silacyclobutene compounds of the present invention wherein $R^4$ and at least one of $R^5$ and $R^6$ are aryl exhibit photoluminescence in the blue region of the visible spectrum.

The aforementioned method of preparing the silacyclobutene compounds of the present invention is highly regioselective. In other words, the present method affords a single regioisomer wherein the vinylic group in the starting conjugated enyne is attached to the ring C-3 position in the silacyclobutene compound. Regioisomeric silacyclobutene compounds having the vinylic group attached to the ring C-2 position are not detected. Moreover, the reaction proceeds in one synthetic step using readily accessible starting materials.

The silane and siloxane polymers of the present invention exhibit improved resistance to low temperatures compared to conventional polysiloxanes and polysilanes. Moreover, the silane and siloxane polymers of the instant invention contain at least one silacyclobutene unit having a vinylic group attached to the ring C-3 position. The carbon—carbon double bond of the vinylic group in the silacyclobutene units is reactive in hydrosilylation reactions with compounds containing silicon-bonded hydrogen atoms. Furthermore, silane and siloxane polymers containing at least one silacyclobutene unit wherein $R^4$ and at least one of $R^5$ and $R^6$ are aryl exhibit photoluminescence in the blue region of the visible spectrum.

The silacyclobutene compounds of the present invention are particularly useful for preparing silane and siloxane polymers, including homopolymers and copolymers. The silacyclobutene compounds of the instant invention having at least one chloro group attached to the ring silicon atom are useful for preparing silane polymers and silylating silica or glass surfaces. The silacyclobutene compounds of the present invention having at least one chloro, triorganosiloxy, or organooxy group attached to the ring silicon atom are useful for preparing siloxane polymers and endcapping siloxane polymers and siloxane resins.

The silacyclobutene compounds of the instant invention having a vinylic group attached to the ring C-3 position can be used in hydrosilylation reactions with compounds having silicon-bonded hydrogen atoms, such as polysiloxanes and polysilanes, to produce polysiloxanes or polysilanes containing terminal and/or pendant silacyclobutene rings.

Additionally, the silacyclobutene compounds of the present invention wherein $R^4$ and at least one of $R^5$ and $R^6$ are aryl exhibit photoluminescence in the blue region of the visible spectrum and can be used to prepare luminescent paints and coatings.

The silane polymers of the present invention are useful for the preparation of silicon carbide by pyrolysis.

The siloxane polymers of the present invention are useful as ingredients in compositions exposed to low temperatures, such as transformer fluids and brake fluids.

The siloxane polymers of the instant invention are also useful for the preparation of hydrosilylation curable silicone compositions, which further comprise an organohydrogensiloxane crosslinking agent.

The silane and siloxane polymers of the present invention containing at least one silacyclobutene unit wherein $R^4$ and at least one of $R^5$ and $R^6$ are aryl exhibit photoluminescence in the blue region of the visible spectrum and can be used to prepare luminescent paints and coatings.

These and other features, aspects, and advantages of the present invention will become better understood with reference to the following description and appended claims.

DETAILED DESCRIPTION OF THE INVENTION

As used herein, the term "vinylic group" refers to a substituted or unsubstituted vinyl group having the formula $-CR^4=CR^5R^6$, wherein $R^4$, $R^5$, and $R^6$ are defined below.

A silacyclobutene compound according to the present invention has the formula:

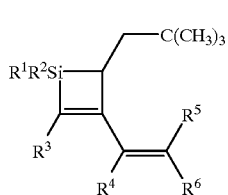

(I)

wherein $R^1$ and $R^2$ are independently chloro, triorganosiloxy, organooxy, triorganosilyl, or a monovalent hydrocarbon group; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl.

The monovalent hydrocarbon groups represented by $R^1$ and $R^2$ typically have 1 to 20 carbon atoms, preferably have 1–10 carbon atoms, and more preferably have 1–5 carbon atoms. Acyclic monovalent hydrocarbon groups containing at least 3 carbon atoms can have a branched or unbranched structure. Examples of monovalent hydrocarbon groups include, but are not limited to, unbranched and branched alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2dimethylpropyl, hexyl, heptyl, octyl, nonyl, decyl, undecyl, dodecyl, tridecyl, tetradecyl, pentadecyl, hexadecyl, heptadecyl, and octadecyl; cycloalkyl, such as cyclopentyl, cyclohexyl, and methylcyclohexyl; aryl, such as phenyl and naphthyl; alkaryl, such as tolyl and xylyl; aralkyl, such as benzyl and phenethyl; alkenyl, such as vinyl, allyl, and propenyl; arylalkenyl, such as styryl and cinnamyl; and alkynyl, such as ethynyl and propynyl. Examples of preferred monovalent hydrocarbon groups include methyl, ethyl, propyl, butyl, and phenyl.

The triorganosiloxy groups represented by $R^1$ and $R^2$ have the formula $R_3SiO-$, wherein each R is independently a monovalent hydrocarbon group as defined and exemplified above, including the preferred embodiments thereof. Examples of preferred triorganosiloxy groups include trimethylsiloxy, triethylsiloxy, dimethylphenylsiloxy, and diphenylmethylsiloxy.

The organooxy groups represented by $R^1$ and $R^2$ have the formula $RO-$, wherein R is a monovalent hydrocarbon group as defined and exemplified above, including the preferred embodiments thereof. Examples of preferred organooxy groups include methoxy, ethoxy, propoxy, butoxy, and phenoxy.

The triorganosilyl groups represented by $R^1$, $R^2$, and $R^3$ have the formula $R_3Si-$, wherein each R is independently a monovalent hydrocarbon group as defined and exemplified above, including the preferred embodiments thereof. Examples of preferred triorganosilyl groups include trimethylsilyl, triethylsilyl, dimethylphenylsilyl, and diphenylmethylsilyl.

The monovalent hydrocarbon groups represented by $R^4$, $R^5$, and $R^6$ are free of conjugated aliphatic unsaturation. As used herein, the term "free of conjugated aliphatic unsaturation" means that the monovalent hydrocarbon groups do not contain an aliphatic carbon—carbon double bond or carbon—carbon triple bond conjugated to the carbon—carbon double bond in the silacyclobutene ring. These monovalent hydrocarbon groups typically have 1 to 20 carbon atoms, preferably have 1–10 carbon atoms, and more preferably have 1–5 carbon atoms. Acyclic monovalent hydrocarbon groups containing at least 3 carbon atoms can have a branched or unbranched structure. Examples of monovalent hydrocarbon groups free of conjugated aliphatic unsaturation include, but are not limited to, unbranched and branched alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, undecyl, dodecyl, tridecyl, tetradecyl, pentadecyl, hexadecyl, heptadecyl, and octadecyl; cycloalkyl, such as cyclopentyl, cyclohexyl, and methylcyclohexyl; aryl, such as phenyl, naphthyl, tolyl and xylyl; and aralkyl, such as benzyl and phenethyl; alkenyl, such as allyl, and 2-butenyl; arylalkenyl, such as cinnamyl; and alkynyl, such as 2-propynyl. Examples of preferred monovalent hydrocarbon groups free of conjugated aliphatic unsaturation include methyl, ethyl, propyl, butyl, and phenyl.

The monovalent hydrocarbon groups represented by $R^3$ are free of conjugated aliphatic unsaturation and cannot be aryl. These monovalent hydrocarbon groups are the same as the monovalent hydrocarbon groups represented by $R^4$, $R^5$, and $R^6$ above, excluding aryl.

The alkanediyl groups represented by $R^4$ and $R^6$ together have 2 to 5 carbon atoms between the terminal free valences. Thus, the alkanediyl group and the two double-bonded carbon atoms to which it is attached form a carbocyclic ring having 4 to 7 carbon atoms. Examples of alkanediyl groups represented by $R^4$ and $R^6$ together include, but are not limited to, ethane-12-diyl, propane-1,3-diyl, and butane-1, 4-diyl. Examples of silacyclobutene compounds of the present invention include, but are not limited to, 1,1-dichloro-4-neoptenyl-2-(trimethylsilyl)-3-vinyl-1-silacyclobut-2-ene; 1,1-dichloro-3-(2-methoxyvinyl)-4-neopentyl-2-(trimethylsilyl)-1-silacyclobut-2-ene; 1,1 dichloro-4-neopentyl-3-(2-phenylvinyl)-2-(trimethylsilyl)-1-silacyclobut-2-enc; 1,1 dichloro-3 -(1-methylvinyl)-4-neopentyl-2-(trimethylsilyl)-1-silacyclobut-2-ene; 1,1 dichloro-4-neopentyl-3 -(1 -phenylvinyl)-2-(trimethylsilyl)-1-silacyclobut-2-ene; 1,1 dichloro-3-(1 -methylprop-1-en-1-yl)-4-neopentyl-2-(trimethylsilyl)-1-silacyclobut-2-ene; 1,1 dichloro-3-(cyclohex-1-en-1-yl)-4-neopentyl-2-(trimethylsilyl)-1-silacyclobut-2-ene; 1,1-dichloro-3 -(cyclohexylidenemethyl)-4-neopentyl-2-(trimethylsilyl)-1-silacyclobut-2-ene; 1,1 dichloro-2-ethyl-3-(1-methylvinyl)-4-neopentyl-1 -silacyclobut-2-ene; and 1,1-dichloro-3-(cyclohex-1-en-1-yl)-2-methyl-4-neopentyl-1-silacyclobut-2-ene.

A method of preparing a silacyclobutene compound according to the present invention comprises contacting a mixture comprising a chlorovinylsilane having the formula:

and a conjugated enyne having the formula:

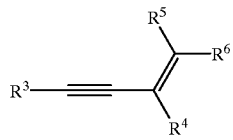

with tert-butyllithium, wherein $R^1$ and $R^2$ are independently chloro or triorganosiloxy; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl.

In the above formula for the chlorovinylsilane, the triorganosiloxy groups represented by $R^1$ and $R^2$ are as defined and exemplified above for the silacyclobutene compound having formula (I), including the preferred embodiments thereof.

In the above formula for the conjugated enyne, the groups represented by $R^3$, $R^4$, $R^5$, and $R^6$ are as defined and exemplified above for the silacyclobutene compound having formula (I), including the preferred embodiments thereof.

The chlorovinylsilanes of the present method having at least one triorganosiloxy group can be prepared by reacting trichlorovinylsilane with the appropriate amount of a triorganosilanol or a triorganosilanoate according to the following scheme:

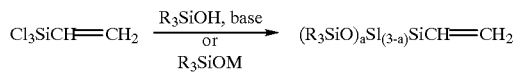

wherein R is a monovalent hydrocarbon group as defined and exemplified above for the silacyclobutene compound having formula (I), M is an alkali metal, and a is 1 or 2. A dichloro(triorganosiloxy)vinylsilane can be obtained by using one mole of the triorganosilanol or triorganosilanoate per mole of trichlorovinylsilane. A chlorodi(triorganosiloxy) vinylsilane can be obtained by using two moles of the triorganosilanol or triorganosilanoate per mole of trichlorovinylsilane. The reaction of the triorganosilanol or triorganosilanoate with trichlorovinylsilane is typically carried out in an ether solvent, such as diethyl ether or tetrahydrofuran. Additionally, the reaction of the triorganosilanol with trichlorovinylsilane is preferably carried out in the presence of a base, such as pyridine or a tertiary amine, which can combine with the liberated HCl.

A preferred method of preparing the triorganosiloxy-containing chlorovinylsilanes of the present method was used by Auner et al. to prepare chlorobis(trimethylsiloxy) vinylsilane (Chem. Ber. 1993, 126, 2177–2186). A solution of a lithium trimethylsilanoate (400 mmol) in diethyl ether (250 mL) is slowly added over a period of three hours to a solution of trichlorovinylsilane (200 mmol) in tetrahydrofuran (300 mL) at 0° C. After allowing the mixture to warm to room temperature, the ether solvents are removed by distillation. The residue is dissolved in n-pentane and the solution is refluxed for eight hours, during which time a lithium chloride precipitate forms. The solution is filtered through a glass frit (D4) to remove the lithium chloride and the filtrate is concentrated by evaporation. The residue is distilled to give chlorobis(trimethylsiloxy)vinylsilane in 64% yield. Dichloro(trimethylsiloxy)vinylsilane can be prepared using the same general procedure and equal amounts (e.g., 200 mmol) of lithium trimethylsilanoate and trichlorovinylsilane.

The conjugated enynes of the present method wherein $R^3$ is a monovalent hydrocarbon group free of conjugated aliphatic unsaturation can be prepared by well known methods in the art, including dehydration of propargylic alcohols, coupling of terminal alkynes with vinyl halides, and isomerization of certain enynes. For example, these and other methods are described by L. Brandsma in Studies in Organic Chemistry 34: Preparative Acetylenic Chemistry, 2nd ed.; Elsevier Science: Amsterdam, 1992. The particular method selected, which depends on the structure of the desired enyne, will be apparent to one skilled in the art. Some of these methods are demonstrated in the Examples below.

The conjugated enynes of the present method wherein $R^3$ is a triorganosilyl group can be prepared by silylation of the corresponding enynes having the formula HC≡CC($R^4$)=CR$^5$R$^6$ according to the following scheme:

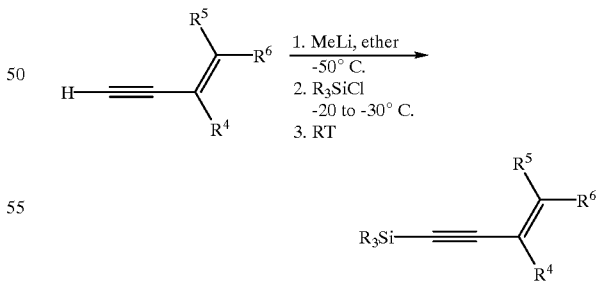

wherein R is a monovalent hydrocarbon group as defined and exemplified above for the silacyclobutene compound having formula (I); and $R^4$, $R^5$, and $R^6$ are as defined and exemplified above for the silacyclobutene compound having formula (I).

In place of methyllithium, other organolithium compounds can be used, including ethyllithium, butyllithium, and phenyllithium.

The enynes having the formula HC≡CC(R⁴)=CR⁵R⁶ can be prepared by well known methods in the art, including dehydration of propargylic alcohols, coupling of terminal alkynes with vinyl halides, and isomerization of certain enynes. For example, these and other methods are described by L. Brandsma in Studies in Organic Chemistry 34: Preparative Acetylenic Chemistry, 2nd ed.; Elsevier Science: Amsterdam, 1992. The particular method selected, which depends on the structure of the desired enyne, will be apparent to one skilled in the art.

The preceding method of preparing conjugated enynes having a triorganosilyl group attached to the terminal triple-bonded carbon atom is described in the Examples below.

The tert-butyllithium of the present method is typically used in a hydrocarbon solvent such as pentane, hexane, or cyclohexane. Methods of preparing tert-butyllithium are very well known in the art. Solutions of tert-butyllithium in hydrocarbon solvents are commercially available in a range of concentrations. Preferably, the hydrocarbon solvent for the tert-butyllithium is the same as the hydrocarbon solvent used as a diluent for the reaction, described below, when a diluent is used.

The silacyclobutene compounds of the present method are prepared by contacting a mixture of the chlorovinylsilane and the conjugated enyne with tert-butyllithium. The reaction can be carried out in any standard reactor suitable for contacting a chlorosilane with an organolithium compound. Preferably, the reactor is equipped with a means of agitation, such as a stirring.

The present method is preferably carried out in the substantial absence of atmospheric oxygen or moisture. This can be accomplished by purging the reactor with a dry inert gas, such as nitrogen or argon, prior to the introduction of the reactants and thereafter maintaining an atmosphere of such gas in the reactor.

Although the silacyclobutene compounds of the present method can be prepared in the absence of a diluent, the chlorovinylsilane and the conjugated enyne are preferably dissolved in a hydrocarbon solvent prior to contacting the resulting mixture with tert-butyllithium. Any hydrocarbon solvent or mixture of hydrocarbon solvents that does not interfere with the reaction to produce the silacyclobutene compounds of the present method can be used as a diluent. Preferably, the hydrocarbon solvent has a normal boiling point up to about 200° C. When the hydrocarbon solvent has a boiling point above about 200° C., it may be difficult to separate the solvent from the silacyclobutene compounds by distillation. Examples of suitable hydrocarbon solvents include, but are not limited to, pentane, hexane, cyclohexane, methylcyclohexane, heptane, octane, toluene, xylene, and isomers thereof. Preferably the hydrocarbon solvent is pentane or hexane. When used, the volume of the hydrocarbon solvent is typically from 0.01 to 100 and preferably 1 to 20 times the combined volume of the chlorovinylsilane and the conjugated enyne.

The mixture of the chlorovinylsilane and the conjugated enyne can be contacted with tert-butyllithium at a temperature of from about −78° C. up to about 70° C. Preferably, the reaction is carried out at a temperature of from −78° C. to room temperature and more preferably, at room temperature.

Typically, the mixture of the chlorovinylsilane and the conjugated enyne is contacted with tert-butyllithium by slowly adding tert-butyllithium to the mixture. Preferably, a solution of tert-butyllithium in a hydrocarbon solvent is added to the mixture in a dropwise manner. Also, preferably, the reaction mixture is agitated, for example, by stirring, at least during the addition of the tert-butyllithium.

Although, the mole ratio of the chlorovinylsilane to the conjugated enyne to tertbutyllithium may vary over a wide range, preferably about equimolar amounts of these reactants are used. An excess of any one of the reactants can lead to the formation of byproducts and a lower yield of the desired silacyclobutene compound. For example, excess tert-butyllithium may react with the silacyclobutene product by displacing chloride or cleaving the triorganosiloxy-silicon bond. Excess conjugated enyne may react with tert-butyllithium to form byproducts, such as 1,2- and 1,4-addition products. Excess chlorovinylsilane may react with the tert-butyllithium to form byproducts such as disilacyclobutanes.

The silacyclobutene compounds of the present method can be recovered from their reaction mixtures by removing the lithium chloride precipitate by filtration, removing the hydrocarbon solvent by simple distillation under reduced pressure, and then fractionally distilling the residue under high vacuum.

The silacyclobutene compounds of the present invention having at least one triorganosiloxy group, organooxy group, triorganosilyl group, or monovalent hydrocarbon group attached to the ring silicon atom can be prepared from the corresponding monochlorosilacyclobutene or dichlorosilacyclobutene compounds using well known reactions of organochlorosilanes to form silicon-oxygen, silicon—silicon, and silicon-carbon bonds. The monochlorosilacyclobutene starting materials can be prepared from the corresponding dichlorosilacyclobutene compounds using these same methods. The dichlorosilacyclobutene compounds are prepared as described above.

The silacyclobutene compounds of the instant invention having at least one triorganosiloxy group attached to the ring silicon atom can be prepared by reacting the corresponding triorganosilanol or triorganosilanoate with a chlorosilacyclobutene compound according to the following scheme:

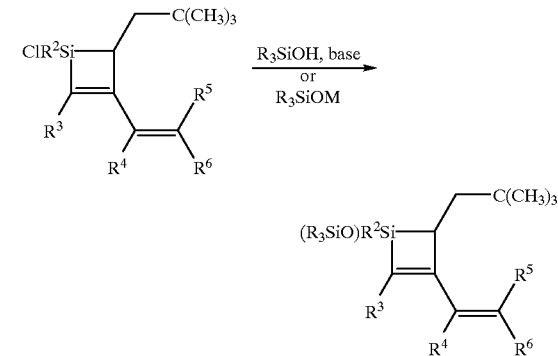

wherein R is a monovalent hydrocarbon group as defined and exemplified above for the silacyclobutene compound having formula (I); M is an alkali metal; and R², R³, R⁴, R⁵, and R⁶ are as defined and exemplified above for the silacyclobutene compound having formula (I); provided that R³ is not aryl.

The reaction of the triorganosilanol with the chlorosilacyclobutene is typically carried out in the presence of a base, such as pyridine or a tertiary amine, which can combine with the liberated HCl.

The triorganosilanoates can be obtained by reacting the corresponding triorgano(organooxy)silanes with an alkali metal hydroxide or by reacting the corresponding triorganosilanols with an alkali metal or alkali metal hydroxide. The triorganosilanoates can also be prepared by reacting the corresponding hexaorganodisiloxanes with sodium hydroxide in alcoholic solution or with an organolithium reagent, such as methyllithium or phenyllithium in a hydrocarbon solvent.

The reaction of the triorganosilanoate with the chlorosilacyclobutene compound is typically carried out in a hydrocarbon solvent such as toluene.

The silacyclobutene compounds of the instant invention having at least one organooxy group attached to the ring silicon atom can be prepared by reacting the corresponding alcohol or phenol with a chlorosilacyclobutene compound in the presence of a base according to the following scheme:

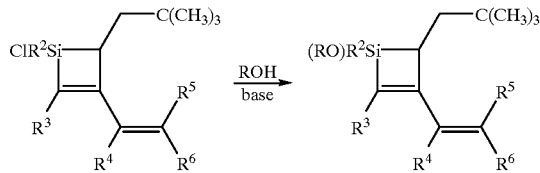

wherein R is a monovalent hydrocarbon group as defined and exemplified above for the silacyclobutene compound having formula (I); and $R^2$, $R^3$, $R^4$, $R^5$, and $R^6$ are as defined and exemplified above for the silacyclobutene compound having formula (I); provided that $R^3$ is not aryl.

The reaction of the alcohol or phenol with the chlorosilacyclobutene compound is typically carried out in the presence of a base, such as pyridine or a tertiary amine, which can combine with the liberated HCl.

Preferably, the alcohol or phenol is substantially free of water. The reaction of the alcohol or phenol with the chlorosilacyclobutene compound is frequently carried out using excess alcohol or phenol as the solvent. However, excess alcohol or phenol should be avoided when preparing a mono(organooxy)silacyclobutene compound from a dichlorosilacyclobutene compound. The reaction of the alcohol or phenol with the chlorosilacyclobutene compound can also be carried out in an inert solvent such as ether or toluene.

The silacyclobutene compounds of the present invention having at least one triorganosilyl group attached to the ring silicon atom can be prepared by reacting the corresponding triorganosilyl-alkali metal compound with a chlorosilacyclobutene compound according to the following scheme:

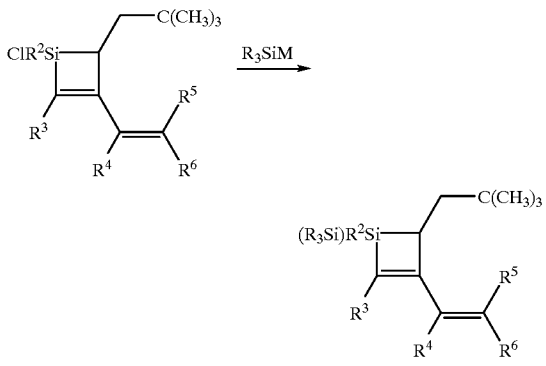

wherein R is a monovalent hydrocarbon group as defined and exemplified above for the silacyclobutene compound having formula (I); M is an alkali metal; and $R^2$, $R^3$, $R^4$, $R^5$, and $R^6$ are as defined and exemplified above for the silacyclobutene compound having formula (I); provided that $R^3$ is not aryl.

The triorganosilyl-alkali metal compounds can be obtained by reacting the corresponding hexaorganodisilanes with an alkali metal in an ether solvent. These compounds can also be prepared in good yield by reacting the corresponding chlorosilanes with lithium metal in tetrahydrofuran.

The reaction of the triorganosilyl-alkali metal compound with the chlorosilacyclobutene compound is typically carried out in an ether solvent, such as tetrahydrofuran, at room temperature.

The silacyclobutene compounds of the present invention having at least one monovalent hydrocarbon group attached to the ring silicon atom can be prepared by reacting the corresponding Grignard reagent or organometallic compound with a chlorosilacyclobutene compound according to the following scheme:

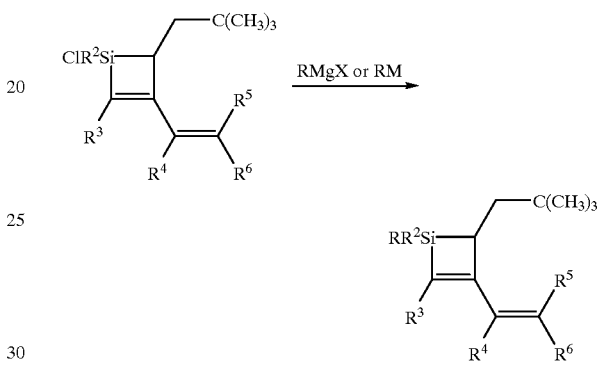

wherein R is a monovalent hydrocarbon group as defined and exemplified above for the silacyclobutene compound having formula (I); M is a metal; X is chloro or bromo; and $R^2$, $R^3$, $R^4$, $R^5$, and $R^6$ are as defined and exemplified above for the silacyclobutene compound having formula (I); provided that $R^3$ is not aryl.

The organometallic compound can be any of the common organometallic compounds that are reactive with organochlorosilanes, including organolithium, organosodium, organopotassium, and organozinc compounds. Organolithium compounds are preferred due to their greater reactivity.

The reaction of the Grignard reagent or organometallic compound with the chlorosilacyclobutene compound is typically carried out in an ether, such as diethyl ether, or a hydrocarbon solvent, such as toluene.

A silane polymer according to the present invention contains at least one silacyclobutene unit having the formula:

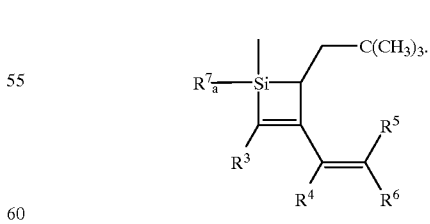

(II)

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; $R^7$ is chloro, triorganosiloxy, organooxy, triorganosilyl, or a monovalent hydrocarbon group; and a is 0 or 1; provided that $R^3$ is not aryl.

In formula (II) above, the groups represented by $R^3$, $R^4$, $R^5$, $R^6$, and $R^7$ are as defined and exemplified above for the silacyclobutene compound having formula (I), including the preferred embodiments thereof. The silane polymers of the present invention have a degree of polymerization typically from 3 to about 1000 and preferably from 5 to about 200.

The silane polymers of the instant invention include, but are not limited to, homopolymers and copolymers containing silacyclobutene units having formula (II). One type of copolymer contains only silacyclobutene units, wherein at least two different silacyclobutene units are present. Another type of copolymer contains silacyclobutene units and organosilane units having the formula $R_2Si$ wherein R is a monovalent hydrocarbon group as defined above for the silacyclobutene compound having formula (I).

The silane polymer of the present invention can be prepared using any of the well known methods of preparing polysilanes from organochlorosilanes. Preferably, the silane polymer of the present invention is prepared using the Wurtz coupling reaction by reacting at least one chlorosilacyclobutene compound, or a mixture of at least one chlorosilacyclobutene compound and an organochlorosilane compound in a hydrocarbon solvent in the presence of sodium (or lithium) metal. Chlorosilacyclobutene compounds suitable for use in preparing the silane polymers of the present invention have formula (I) wherein at least one of $R^1$ and $R^2$ is chloro. Organochlorosilane compounds suitable for use in the Wurtz coupling reaction include, but are not limited to, compounds having the formula $R_mSiCl_{(4-m)}$ and silane oligomers and silanc polymers containing at least one silicon-bonded chlorine atom, wherein R and the organic groups in the oligomers and polymers are monovalent hydrocarbon groups as defined above for the silacyclobutene compound having formula (I), and m is 2 or 3.

Preferably, the Wurtz reaction is carried out in a hydrocarbon solvent having a boiling point above about 100° C., such as toluene, under reflux conditions. The polymer product can be recovered by removing the sodium (or lithium) chloride by filtration and then concentrating the filtrate under reduced pressure.

A siloxane polymer according to the present invention contains at least one silacyclobutene unit having the formula:

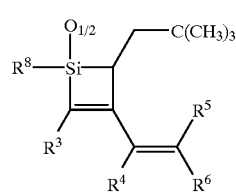

(III)

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; and $R^8$ is chloro, triorganosiloxy, organooxy, triorganosilyl, a monovalent hydrocarbon group, hydroxy, or —O—; provided that $R^3$ is not aryl.

In formula (III) above, the groups represented by $R^3$, $R^4$, $R^5$, $R^6$, and $R^8$ are as defined and exemplified above for the silacyclobutene compound having formula (I), including the preferred embodiments thereof. The siloxane polymers of the present invention have a degree of polymerization typically from 3 to about 1000 and preferably from 5 to about 200.

The siloxane polymers of the instant invention include, but are not limited to, homopolymers and copolymers containing silacyclobutene units having formula (III). One type of copolymer contains only silacyclobutene units, wherein at least two different silacyclobutene units are present. Another type of copolymer contains silacyclobutene units and organosiloxane units having the formula $R_2SiO_{2/2}$ wherein R is a monovalent hydrocarbon as defined above for the silacyclobutene compound having formula (I).

The siloxane polymers of the present invention can be prepared using any of the well known methods of preparing siloxane polymers, including hydrolysis and equilibration. For example, the siloxane polymers of the instant invention can be prepared by hydrolyzing at least one chlorosilacyclobutene compound, or a mixture of at least one chlorosilacyclobutene compound and an organochlorosilane compound. Chlorosilacyclobutene compounds suitable for use in preparing the siloxane polymers of the present invention by hydrolysis have formula (I) wherein at least one of $R^1$ and $R^2$ is chloro. Organochlorosilane compounds suitable for use in the hydrolysis reaction include, but are not limited to, compounds having the formula $R_mSiCl_{(4-m)}$ and siloxane oligomers and siloxane polymers containing at least one silicon-bonded chlorine atom, wherein R and the organic groups in the oligomers and polymers are monovalent hydrocarbon groups as defined above for the silacyclobutene compound having formula (I), and m is 2 or 3.

The siloxane polymers of the present invention can also be prepared by hydrolyzing at least one (organooxy) silacyclobutene compound, or a mixture of at least one (organooxy)silacyclobutene compound and an organo (organooxy)silane compound. (Organooxy)silacyclobutene compounds suitable for use in preparing the siloxane polymers of the present invention by hydrolysis have formula (I) wherein at least one of $R^1$ and $R^2$ is organooxy. Organo (organooxy)silane compounds suitable for use in the hydrolysis reaction include, but are not limited to, compounds having the formula $R_mSi(OR)_{4-m}$ and siloxane oligomers and polymers containing at least one silicon-bonded organooxy group, wherein R and the organic groups in the oligomers and polymers are monovalent hydrocarbon groups as defined above for the silacyclobutene compound having formula (I), and m is 2 or 3.

The hydrolysis of the (organooxy)silacyclobutene compounds can be carried out in the presence of an acid or base catalyst. Acid catalysts which can be removed by washing, such as hydrochloric acid, oxalic acid, acetic acid, and trichloracetic acid are preferred.

The siloxane polymers of the present invention can also be prepared by equilibration of at least one (triorganosiloxy) silacyclobutene compound, or a mixture of at least one (triorganosiloxy)silacyclcobutene compound and an organosiloxane compound. Triorganosiloxysilacyclobutene compounds suitable for use in preparing the siloxane polymers of the present invention have formula (I) wherein at least one of $R^1$ and $R^2$ is triorganosiloxy. The organosiloxane compounds used in the equilibration reaction can be any common organosiloxane compounds, including disiloxanes having the formula $(R_3-Si)_2O$, organocyclosiloxanes having the formula $(R_2SiO)_n$, siloxane oligomers, and siloxane polymers, wherein R and the organic groups in the oligomers and polymers are monovalent hydrocarbon groups as defined above for the silacyclobutene compound having formula (I), and n is from 3 to about 10. Examples of organocyclosiloxanes include, but are not limited to, octamethyltetracyclosiloxane ($D_4$) and decamethylpentacyclosiloxane ($D_5$). Examples of siloxane oligomers and polymers include, but are not limited to, dimethylsiloxane fluids.

The aforementioned equilibration reaction is typically carried out in the presence of a strong acid or base. Examples of suitable acids include, but are not limited to, sulfuric acid, trifluormethanesulfonic acid, and dodecylbenzenesulfonic acid. Examples of suitable bases include, but are not limited to, potassium hydroxide and tetrabutylammonium hydroxide.

The silacyclobutene compounds of the present invention exhibit high thermal stability. In fact, the compounds can be heated in an air atmosphere at temperatures up to 200° C. without any decomposition. Additionally, the silacyclobutene compounds of the instant invention wherein $R^4$ and at least one of $R^5$ and $R^6$ are aryl exhibit photoluminescence in the blue region of the visible spectrum.

The aforementioned method of preparing the silacyclobutene compounds of the present invention is highly regioselective. In other words, the present method affords a single regioisomer wherein the vinylic group from the starting conjugated enyne is attached to the ring C-3 position in the silacyclobutene compound. Regioisomeric silacyclobutene compounds having the vinylic group attached to the ring C-2 position are not detected. Moreover, the reaction proceeds in one synthetic step using readily accessible starting materials.

The silane and siloxane polymers of the present invention exhibit improved resistance to low temperatures compared to conventional polysiloxanes and polysilanes. Moreover, the silane and siloxane polymers of the instant invention contain at least one silacyclobutene unit having a vinylic group attached to the ring C-3 position. The carbon—carbon double bond of the vinylic group in the silacyclobutene units is reactive in hydrosilylation reactions with compounds containing silicon-bonded hydrogen atoms. Furthermore, silane and siloxane polymers containing at least one silacyclobutene unit wherein $R^4$ and at least one of $R^5$ and $R^6$ are aryl exhibit photoluminescence in the blue region of the visible spectrum.

The silacyclobutene compounds of the present invention are particularly useful for preparing silane and siloxane polymers, including homopolymers and copolymers. The silacyclobutene compounds of the instant invention having at least one chloro group attached to the ring silicon atom are useful for preparing silane polymers and silylating silica or glass surfaces. The silacyclobutene compounds of the present invention having at least one chloro, triorganosiloxy, or organooxy group attached to the ring silicon atom are useful for preparing siloxane polymers and endcapping siloxane polymers and siloxane resins.

The silacyclobutene compounds of the instant invention having a vinylic group attached to the ring C-3 position can be used in hydrosilylation reactions with compounds having silicon-bonded hydrogen atoms, such as polysiloxanes and polysilanes, to produce polysiloxanes or polysilanes containing terminal and/or pendant silacyclobutene rings.

Additionally, the silacyclobutene compounds of the present invention wherein $R^4$ and at least one of $R^5$ and $R^6$ are aryl exhibit photoluminescence in the blue region of the visible spectrum and can be used to prepare luminescent paints and coatings.

The silane polymers of the present invention are useful for the preparation of silicon carbide by pyrolysis.

The siloxane polymers of the present invention are useful as ingredients in compositions exposed to low temperatures, such as transformer fluids and brake fluids.

The siloxane polymers of the instant invention are also useful for the preparation of hydrosilylation curable silicone compositions, which further comprise an organohydrogensiloxane crosslinking agent.

The silane and siloxane polymers of the present invention containing at least one silacyclobutene unit wherein $R^4$ and at least one of $R^5$ and $R^6$ are aryl exhibit photoluminescence in the blue region of the visible spectrum and can be used to prepare luminescent paints and coatings.

EXAMPLES

The following examples are presented to further illustrate the silacyclobutene compounds and methods of the present invention, but are not to be considered as limiting the invention, which is delineated in the appended claims. All parts and percentages reported in the examples are by weight.

Air and/or moisture sensitive reactions were carried out under a nitrogen or argon atmosphere. The nitrogen and argon were dried over copper catalyst and molecular sieves (4 Å). The solvents were dried by distillation according to conventional procedures. Chlorosilanes were distilled from $K_2CO_3$ prior to use. Reactions at temperatures below 0° C. were carried out using a cooling bath consisting of an ethanol/dry ice or ethanol/liquid nitrogen mixture, unless indicated otherwise.

Gas chromatography was performed using a Chrompack CP 9000 gas chromatograph equipped with a 0.25 mm×10 m Chrompack CP Sil 5 CB capillary column. Gas chromatography, in addition to NMR spectrometry, was used to determine the ratio of the Z to E isomers for the silacyclobutenes in Examples 2 and 3 and the ratio of the Z to F isomers for the silacyclobutanes in Examples 4 and 9.

Nuclear magnetic resonance (NMR) spectra were obtained using a Bruker WP100SY ($^1H$, $^{13}C$), Jeol JNM GX 270 ($^{13}C$, $^{29}Si$), Bruker AMX 300 ($^{29}Si$), and a Bruker DPX 300 ($^1H$, $^{13}C$). The NMR solvent was deuterated chloroform, $CDCl_3$, containing tetramethylsilane as an internal standard.

Mass spectra were obtained using a Chrompack 9000 gas chromatograph coupled with a Finnigan MAT ion trap 800. Mass spectral data was collected over a mass to charge (m/z) range of 50 to 600 employing an electron flow of 300 mA, ion accelerating voltage of 3 kV, ionization potential of 70 eV, and source temperature 250° C. Methanol was used as the reactant gas in chemical ionization (CI).

Example 1

Freshly powdered KOH (85%, 300 g) and high-boiling petroleum ether (b.p. >150° C.) were placed in a flask. Stirring was started and 5 g of methyl trioctylammonium chloride (75% aqueous solution) and 5 g of pinacol were added. The mixture was heated for 30 min in an oil bath at 120° C., then 1,4-dichloro-2-butene (trans-isomer, 0.50 mol) was added dropwise over 25 min. A slow stream of $N_2$ (~300 mL/min) was passed through the apparatus. The vinylacetylene condensed in two traps cooled at −78° C. After the addition, the temperature of the oil bath was gradually raised over 30 min to 135° C. Stirring and introduction of $N_2$ were continued for another 1 h. The yield of pure (>95%) vinylacetylene, $HC\equiv CCH=CH_2$, is usually higher than 75%.

To a solution of vinylacetylene in diethyl ether was added 0.95 equivalents (based on the number of moles of vinylacetylene) of methyllithium (1.6 M in diethyl ether) dropwise at −50° C. under nitrogen. Then an equimolar amount of chlorotrimethylsilane was added to the mixture at −20 to −30° C., whereupon precipitation of lithium chloride occurred. The reaction mixture was allowed to warm slowly to room temperature in the cold bath. The diethyl ether was then removed by distillation and the residue was extracted with n-pentane. The extract was filtered through a glass frit (D4) to remove the lithium chloride and the filtrate was concentrated under reduced pressure. The resulting residue was distilled under high vacuum to give a conjugated enyne having the formula:

(A)

Tert-butyllithium in pentane (1.7 M, 29.4 mL, 50 mmol) was added dropwise to a stirred solution of trichlorovinylsilane (8.1 g, 6.4 mL, 50 mmol) and an equimolar amount of conjugated enyne (A) in pentane (100 mL) at 20° C. under nitrogen, whereupon precipitation of lithium chloride occurred. The mixture was stirred overnight and then filtered through a glass frit (D4) to remove the lithium chloride. The filtrate was concentrated under reduced pressure and the resulting residue was fractionally distilled through a vacuum-jacketed 40-cm vigreaux column under high vacuum (1 Pa) to give 4.46 g (14.5 mmol, 29%) of a colorless liquid (bp 85° C./1 Pa) consisting of 1,1-dichloro4-neoptenyl-2-(trimethylsilyl)-3-vinyl-1-silacyclobut-2-ene, having the formula:

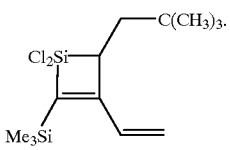

(1)

The NMR spectra ($^1$H, $^{13}$C, and $^{29}$Si) obtained for the reaction product are consistent with the silacyclobutenc compound represented by formula (I).

Example 2

A solution of 1.0 mol of butynediol in 160 ml of water was placed in a flask. Sodium hydroxide pellets (100 g) and dimethyl sulfate (2.5 mol) were added in turn in ~20 equal portions over 1.5 h. During the addition, the temperature of the reaction mixture was kept between 30 and 40° C. (occasional cooling). After the addition, the mixture was heated for an additional 3 h in a bath at 90° C. Ice water (150 mL) was then added and, after cooling to 20° C., five extractions with Et$_2$O were carried out. The unwashed organic solutions were dried over K$_2$CO$_3$, after which they were concentrated in vacuo. Distillation of the remaining liquid through a 40-cm Vigreaux column gave the bis-ether CH$_3$OCH$_2$C≡CCH$_2$OCH$_3$ (b.p. 54° C./12 mm Hg) in a yield of at least 80%.

The bis-ether CH$_3$OCH$_2$C≡CCH$_2$OCH$_3$ (0.50 mol) was added dropwise over 30 min to a suspension of 1.2 mol of sodamide in 1 L of liquid ammonia. After the addition, the flask was placed in a water bath at 40° C. When most of the ammonia was evaporated, 250 mL of Et$_2$O was added. The flask was placed in a bath of ice water and ice water (500 mL) was added to the reaction mixture over about 15 min, while introducing N$_2$. During this hydrolysis operation, the mixture was vigorously stirred. After disappearance of all solid material, the layers were separated and the aqueous layer was extracted five times with small portions of Et$_2$O. The organic solutions were washed with saturated aqueous NH$_4$Cl and subsequently dried over MgSO$_4$, after which most of the Et$_2$O was distilled off through a 40-cm Vigreaux column, keeping the bath temperature below 80° C. After cooling to room temperature, the enyne ether was isolated by distillation in vacuo using a single receiver, cooled at 0° C. Methoxybutenyne, HC≡CCH=CHOCH$_3$, was obtained as a mixture of E and Z isomers.

The enyne HC≡CCH=CHOCH$_3$ was treated with methyllithium and chlorotrimethylsilane using the method in Example 1 to give a conjugated enyne having the formula:

(B)

A solution of trichlorovinylsilane and an equimolar amount of conjugated enyne (B) in pentane was treated with tert-butyllithium using the method in Example 1. The residue was distilled under high vacuum (0.1 Pa) to give 9.51 g (28.2 mmol, 56%) of a colorless viscous liquid (bp 78° C./0.1 Pa) consisting of 1,1-dichloro-3-(2-methoxyvinyl)-4neopentyl-2-(trimethylsilyl)-1-silacyclobut-2-ene, having the formula:

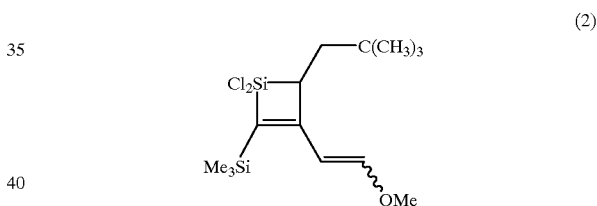

(2)

as a mixture of Z and E isomers. The mole ratio of the Z isomer (silacyclobutene ring and OMe group on same side of carbon—carbon double bond) to the E isomer isomer (silacyclobutene ring and OMe group on opposite sides of carbon—carbon double bond) was 16:84, as determined by gas chromatography and NMR spectrometry.

The NMR spectra ($^1$H, $^{13}$C, and $^{29}$Si), mass spectra, and elemental analysis obtained for the reaction products are consistent with the silacyclobutene compounds represented by formula (2).

Example 3

To a solution of 0.30 mol of lithium acetylide in 200 mL of DMSO was added freshly distilled styrene oxide (0.20 mol) dropwise over 15 min, while keeping the temperature between 20 and 30° C. After stirring the mixture for an additional 2 h at 25° C., 500 mL of ice water was added and six extractions with Et$_2$O were carried out. After washing the extracts with water and drying them over MgSO$_4$, the solvent was removed under reduced pressure. Distillation of the remaining liquid through a short column gave the acetylenic alcohol HC≡CCH$_2$CH(OH)Ph (b.p. 120° C./1 mm Hg) in ~70% yield.

A mixture of 0.25 mol of HC≡CCH$_2$CH(OH)Ph, 350 mL of Et$_2$O and 0.35 mol (excess) of tosyl chloride was placed in a flask. After dissolution of the tosyl chloride, the solution was cooled to −5° C. (dry-ice/acetone bath). Freshly powdered KOH (140 g) was added in 5-g portions over 15 min to the vigorously stirred mixture while maintaining the temperature between −10 and 0° C. The air was then completely replaced by nitrogen and the cooling bath was removed. At about 15° C. an exothermic reaction started, and after an additional 10 to 15 min the ether began to reflux. The mixture was heated for another hour under reflux. After cooling to room temperature, the thick slurry was poured into 500 mL of ice water and the flask was rinsed with a small amount of ice water. After vigorous shaking and separation of the layers, the aqueous layer was extracted three times with small portions of $Et_2O$. The combined organic solutions were washed with saturated aqueous ammonium chloride and subsequently dried over $MgSO_4$. The greater part of the $Et_2O$ was then distilled off (under a slow stream of $N_2$) at atmospheric pressure through a 40-cm Widmer column. The temperature of the heating bath was kept between 80 and 90° C. during the last stage of this distillation. After cooling to 20° C., the remaining liquid was carefully distilled in a partial vacuum, giving the enyne HC≡CCH═CHPh (Z/E ratio ~55:45; b.p. ~55° C./0.4 mm Hg).

The enyne HC≡CCH═CHPh was treated with methyllithium and chlorotrimethylsilane using the method in Example 1 to give a conjugated enyne having the formula:

(C)

A solution of trichlorovinylsilane and an equimolar amount of conjugated enyne (C) in pentane was treated with tert-butyllithium using the method in Example 1. The residue was distilled under high vacuum (0.07 Pa) to give 13.99 g (36.5 mmol, 73%) of a colorless liquid (bp 81–84° C./0.07 Pa) consisting of 1,1 dichloro-4-neopentyl-3-(2phenylvinyl)-2-(trimethylsilyl)-1-silacyclobut-2-ene, having the formula:

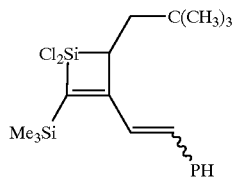

(3)

as a mixture of Z and E isomers. The mole ratio of the Z isomer (silacyclobutene ring and Ph group on same side of carbon—carbon double bond) to the E isomer (silacyclobutene ring and Ph group on opposite sides of carbon—carbon double bond) was 76:24, as determined by gas chromatography and NMR spectrometry.

The NMR spectra ($^1H$ $^{13}C$, and $^{29}Si$) mass spectra, and elemental analysis obtained for the reaction products are consistent with the silacyclobutene compounds represented by formula (3).

Example 4

A flask was charged with 1.3 mol of acetic anhydride and 7 g of p-toluenesulfonic acid monohydrate. The acetylenic alcohol HC≡CC(CH₃)₂OH (1.0 mol) was added over 10 min with some cooling. The flask was then quickly heated until the enyne began to distill out. Further heating was carried out in a controlled way, so that the enyne did not distill too fast: the greater part passed over below 60° C. As the bath temperature was increased the reaction mixture turned very dark. When, after 45–60 min, the temperature in the head of the column had reached 100° C., heating was stopped. The distillate was washed twice in a small separatory funnel with 10–15 mL of cold 3 N KOH solution, in order to remove traces of acetic acid. Redistillation from 5 g of anhydrous $MgSO_4$ gave pure isopropenylacetylene, HC≡CC(CH₃)═CH₂ (b.p. ~35° C./760 mmHg), in excellent yield. The compound was stored in a freezer (−20 to −30° C.).

The enyne HC≡CC(CH₃)═CH₂ was treated with methyllithium and chlorotrimethylsilane using the method in Example 1 to give a conjugated enyne having the formula:

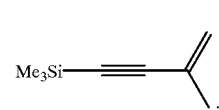

(D)

A solution of trichlorovinylsilane and an equimolar amount of conjugated enyne (D) in pentane was treated with tert-butyllithium using the method in Example 1. The residue was distilled under high vacuum (0.1 Pa) to give a colorless liquid (bp 55–59° C./0.1 Pa) consisting of a mixture of 4.66 g (14.5 mmol, 29%) of 1,1 dichloro-3-(1-methylvinyl)-4neopentyl-2-(trimethylsilyl)-1-silacyclobut-2-ene, having the formula:

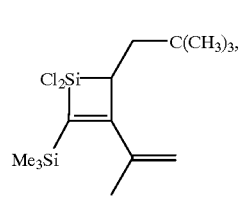

(4)

3.98 g (12.4 mmol, 25%) of Z-1,1-dichloro-3-methyl-2-ncopentyl-3-(2trimethylsilyethynyl)-1-silacyclobutane and 2.70 g (8.4 mmol, 17%) of E-1,1-dichloro-3-methyl-2-neopentyl-3-(2-trimethylsilylethynyl)-1-silacyclobutane. The ratio of the Z isomer (neopentyl group and trimcthyl-silylethynyl group on same side of silacyclobutane ring) to the E isomer (neopentyl group and trimethylsilylethynyl group on opposite sides of silacyclobutane ring) was 59:41, as determined by gas chromatography and NMR sprectrometry.

The NMR spectra ($^1H$, $^{13}C$, and $^{29}Si$), mass spectra, and elemental analysis obtained for the reaction products are consistent with the silacyclobutene compound represented by formula (4) and the silacyclobutane compounds named above.

Example 5

A solution of 2-bromo-2-phenyl-1-ethene (1 equiv), triethylamine (1.2 equiv), and $Pd(PPh_3)_2Cl_2$ (5 mol %) in acetonitrile (approx. 0.1 M) as deaerated with argon, followed by addition of (trimethylsilyl)acetylene (2.5 equiv). The mixture was refluxed until all the bromide was consumed (monitored by TLC/hexane). On cooling the mixture was quenched with water and extracted thoroughly with ethyl ether. Evaporation of the dried (magnesium sulfate) extracts gave a residue which was purified by flash chromatography to give a conjugated enyne having the formula:

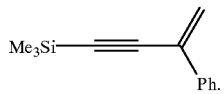
(E)

A solution of trichlorovinylsilane and an equimolar amount of conjugated enyne (E) in pentane was treated with tert-butyllithium using the method in Example 1. The residue was distilled under high vacuum (0.007 Pa) to give 1.73 g (4.5 mmol, 9%) of a colorless liquid (bp 93° C./0.007 Pa) consisting of 1,1 dichloro-4-neopentyl-3-(1-phenylvinyl)-2 (trimethylsilyl)-1-silacyclobut-2-ene, having the formula:

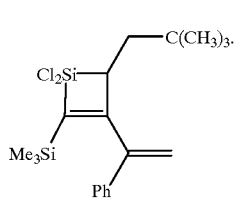
(5)

The NMR spectra ($^1H$, $^{13}C$, and $^{29}Si$), mass spectra, and elemental analysis obtained for the reaction product are consistent with the silacyclobutene compound represented by formula (5).

Example 6

$HC\equiv CC(CH_3)=CH(CH_3)$ was prepared by treating $HC\equiv CC(CH_3)(OH)CH_2CH_3$ with acetic anhydride in the presence of p-toluenesulfonic acid according to the method in Example 4. The enyne $HC\equiv CC(CH_3)=CH(CH_3)$ was treated with methyllithium and chlorotrimethylsilane using the method in Example 1 to give a conjugated enyne having the formula:

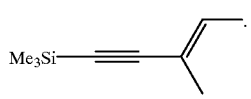
(F)

A solution of trichlorovinylsilane and an equimolar amount of conjuagated enyne (F) in pentane was treated with tert-butyllithium using the method in Example 1. The residue was distilled under high vacuum (0.1 Pa) to give 13.05 g (36.8 mmol, 74%) of a colorless liquid (bp 60–63° C./0.1 Pa) consisting of 1,1 dichloro-3-(1-methylprop-1-en-1-yl)-4neopentyl-2-(trimethylsilyl)-1-silacyclobut-2-ene, having the formula:

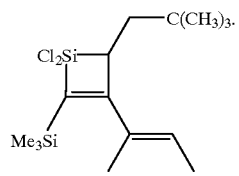
(6)

The NMR spectra ($^1H$, $^{13}C$, and $^{29}Si$), mass spectra, and elemental analysis obtained for the reaction product are consistent with the silacyclobutene compound represented by formula (6).

Example 7

A mixture of 0.5 mol of ethynylcyclohexanol and 90 mL of pyridine was heated to 100° C. A mixture of 33 mL of phosphoryl chloride and 40 mL of pyridine was then added over 15 min, while stirring at a moderate rate. The temperature of the reaction mixture was kept between 105 and 110° C. by occasional cooling or temporarily increasing the rate of stirring. After the addition, heating at 105–110° C. was continued for 15 min. The mixture was cooled to below 75° C. (partial solidification), and 400 mL of ice water was poured into the flask. After vigorous stirring, the layers were separated and five to seven extractions with small portions of a 1:1 mixture of $Et_2O$ and pentane were carried out. The combined organic layers were washed with cold 3 N hydrochloric acid in order to remove pyridine. After drying over $MgSO_4$, the greater part of the solvent was distilled off at atmospheric pressure through a 40-cm Vigreaux column. Distillation of the remaining liquid in vacuo (using a single receiver cooled in an ice bath) gave 1-ethynylcyclohexene (b.p. 38° C./12 mm Hg) in excellent yield.

1-Ethynylcyclohexene was treated with methyllithium and chlorotrimethylsilane using the method in Example 1 to give a conjugated enyne having the formula:

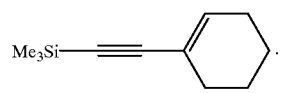
(G)

A solution of trichlorovinylsilane and an equimolar amount of conjugated enyne (G) in pentane was treated with tert-butyllithium using the method in Example 1. The residue was distilled under high vacuum (0.02 Pa) to give 12.11 g (33.5 mmol, 67%) of a white solid (bp 88–89° C./0.02 Pa) consisting of 1,1 dichloro-3-(cyclohex-1-en-1-yl)-4-neopentyl-2-(trimethylsilyl)-1-silacyclobut-2-ene, having the formula:

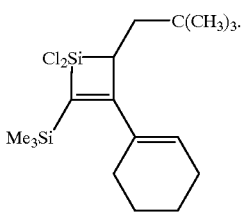
(7)

The NMR spectra ($^1Hi$, $^{13}C$, and $^{29}Si$), mass spectra, and elemental analysis obtained for the reaction product are consistent with the silacyclobutene compound represented by formula (7).

Example 8

1-(1-propynyl)cyclohexene was prepared by treating 1-(1-propynyl)cyclohexanol with phosphoryl chloride in pyridine using the method in Example 7 for preparing 1ethynylcyclohexene.

To a solution of 0.7 mol of sodium amide in about 700 mL of liquid ammonia was added 1-(1-propynyl)cyclohexene (0.50 mol) dropwise over 15 min with efficient stirring. A fine, white suspension of the potassium alkynylide was formed gradually. After 2 h, 200 mL of $Et_2O$ was added over a few minutes. The flask was then placed in a water bath at 40° C. When the stream of ammonia vapor had become faint, introduction of nitrogen (~500 mL/min) was started. An additional volume of 100 mL of $Et_2O$ was added. The flask was placed in an ice-water bath and ice water (~300 mL) was added to the reaction mixture over about half an hour with vigorous stirring. After dissolution of all solid material, the layers were separated and the aqueous layer was extracted twice with small portions of $Et_2O$. The combined organic solutions was dried over MgSO4. Propynylidenecyclohexane (b.p. 55° C./10 mm Hg) was obtained in excellent yield by concentrating the ethereal solution in a water-pump vacuum (bath temperature not higher than 35° C.) and subsequently distilling the remaining liquid thorough a 30-cm Vigreaux column.

The propynylidenecyclohexane was treated with methyllithium and chlorotrimethylsilane using the method in Example 1 to give a conjugated enyne having the formula:

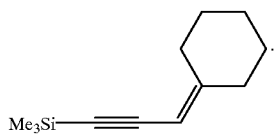

(H)

A solution of trichlorovinylsilane and an equimolar amount of conjuaged enyne (H) in pentane was treated with tert-butyllithium using the method in Example 1. The residue was distilled under high vacuum (0.01 Pa) to give 12.58 g (33.5 mmol, 67%) of a white solid (bp 83–84 C/0.01 Pa) consisting of 1,1-dichloro-3-(cyclohexylidenemethyl)-4neopentyl-2-(trimethylsilyl)-1-silacyclobut-2-ene, having the formula:

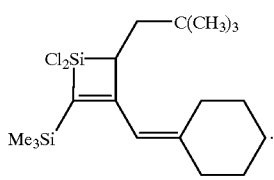

(8)

The NMR spectra ($^1H$, $^{13}C$, and $^{29}Si$), mass spectra, and elemental analysis obtained for the reaction product are consistent with the silacyclobutene compound represented by formula (8).

Example 9

A solution of trichlorovinylsilane and an equimolar amount of 2-methylhex-1-en-3-yne (commercially available from Lancaster, Windham, N.H.), having the formula:

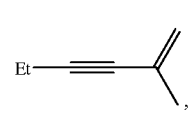

(I)

in pentane was treated with tert-butyllithium using the method in Example 1. The residue was distilled under high vacuum (0.1 Pa) to give a colorless liquid (bp 82–96° C./0.1 Pa) consisting of 2.60 g (9.4 mmol, 19%) of 1,1 dichloro-2-ethyl-3-(1-methylvinyl)-4-neopentyl-1-silacyclobut-2-ene, having the formula:

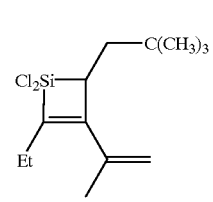

(9)

and 4.46 g (16.1 mmol, 32%) of 3-(but-1-yn-1-yl)-1,1-dichloro-3-methyl-2-neopentyl-1-silacyclobutane as a mixture of Z an E isomers. The ratio of the Z isomer (butynyl group and neopentyl group on same side of silacyclobutane ring) to the E isomer (butynyl group and neopentyl group on opposite sides of silacyclobutane ring) was 53:47, as determined by gas chromatography and NMR sprectrometry.

The NMR spectra ($^1H$, $^{13}C$, and $^{29}Si$), mass spectra, and elemental analysis obtained for the reaction products are consistent with the silacyclobutene compound represented by formula (9) and the silacyclobutane compounds named above.

Example 10

1-ethynylcyclohexene (1.0 mol), prepared as described in Example 7, was added dropwise to a suspension of sodium amide (1.0 mol) in liquid ammonia (1.2 L) at −40 to −50° C. over about 30 min with efficient stirring. During the addition, the temperature of the reaction mixture was maintained at −35 to −45° C. After about 10 min, methyl iodide (1.0 mol) was introduced over 30 min, while keeping the temperature at about −40° C. Fifteen min after the addition was completed, 250 mL of pentane was added with stirring. The reaction mixture was poured onto about 1.5 kg of crushed ice. After melting of the ice and separation of the layers, three extractions with small amounts of pentane were carried out. The organic solutions were washed with dilute HCl and subsequently dried over MgSO4. The greater part (70%) of the solvent was distilled off under nitrogen through a 40-cm Vigreaux column, keeping the bath temperature below 80° C. The remaining liquid was cooled to give light-brown crystals consisting of a conjugated enyne having the formula:

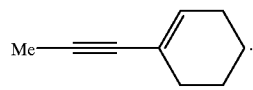 (J)

A solution of trichlorovinylsilane and an equimolar amount of conjuaged enyne (J) in pentane was treated with tert-butyllithium using the method in Example 1. The residue was distilled under high vacuum (0.1 Pa) to give 6.82 g (22.5 mmol, 45%) of a white solid (bp 110° C./0.1 Pa) consisting of 1,1-dichloro-3-(cyclohex-1-en-1-yl)-2-methyl-4-neopentyl-1-silacyclobut-2-ene, having the formula:

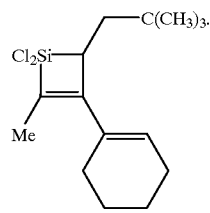 (10)

The NMR spectra ($^1$H, $^{13}$C, and $^{29}$Si), mass spectra, and elemental analysis obtained for the reaction product are consistent with the silacyclobutene compound represented by formula (10).

That which is claimed is:

1. A silacyclobutene compound having the formula:

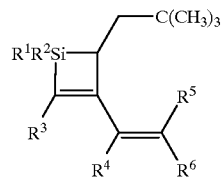

wherein $R^1$ and $R^2$ are independently chloro, triorganosiloxy, organooxy, triorganosilyl, or a monovalent hydrocarbon group; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; provided that $R^3$ is not aryl.

2. The silacyclobutene compound according to claim 1, wherein $R^1$ and $R^2$ are chloro.

3. The silacyclobutene compound according to claim 1, wherein $R^3$ is triorganosilyl.

4. The silacyclobutene compound according to claim 3, wherein $R^3$ is trimethylsilyl.

5. The silacyclobutene compound according to claim 1, wherein $R^4$ and $R^6$ together are ethane-1,2-diyl, propane-1,3-diyl, or butane-1,4-diyl.

6. The silacyclobutene compound according to claim where in $R^4$ and at least one of $R^5$ and $R^6$ are aryl.

7. A method of preparing a silacyclobutene compound, comprising contacting a mixture comprising a chlorovinylsilane having the formula:

$R^1R^2ClSiCH=CH_2$ 

and a conjugated enyne having the formula:

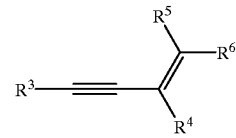

with tert-butyllithium, wherein $R^1$ and $R^2$ are independently chloro or triorganosiloxy; $R^3$ is a monovalent hydrocarbon group free of conjugated aliphatic unsaturation or triorganosilyl; $R^5$ is hydrogen or a monovalent hydrocarbon group free of conjugated aliphatic unsaturation; and $R^4$ and $R^6$ are independently hydrogen or a monovalent hydrocarbon group free of conjugated aliphatic unsaturation or together are an alkanelyl group, wherein the alkanediyl group and the carbon atoms to which it is attached form a carbocyclic ring having 4 to 7 carbon atoms; provided that $R^3$ is not aryl.

8. The method according to claim 7, wherein the step of contacting the mixture of the chlorovinylsilane and the conjugated enyne is carried out in a hydrocarbon solvent.

9. The method according to claim 8, wherein the hydrocarbon solvent is pentane or hexane.

10. The method according to claim 7, wherein the step of contacting the mixture of the chlorovinylsilane and the conjugated enyne is carried out at a temperature of from −78° C. to room temperature.

11. The method according to claim 7, wherein the mole ratio of the chlorovinylsilane to the conjugated enyne to tert-butyllithium is about 1:1:1.

12. A silane polymer containing at least one silacyclobutene unit having the formula:

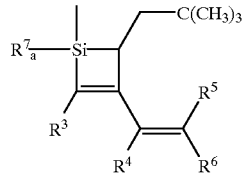

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; $R^7$ is chloro, triorganosiloxy, organooxy, triorganosilyl, or a monovalent hydrocarbon group; and a is 0 or 1; provided that $R^3$ is not aryl.

13. The silane polymer according to claim 12, wherein the polymer is a homopolymer.

14. The silane polymer according to claim 12, wherein the polymer is a copolymer.

15. The silane polymer according to claim 12, wherein $R^3$ is triorganosilyl.

16. The silane polymer according to claim 15, wherein $R^3$ is trimethylsilyl.

17. The silane polymer according to claim 12, wherein $R^4$ and $R^6$ together are ethane-1,2-diyl, propane-1,3-diyl, or butane-1,4-diyl.

18. The silane polymer according to claim 12, wherein $R^4$ and at least one of $R^5$ and $R^6$ are aryl.

19. A siloxane polymer containing at least one silacyclobutene unit having the formula:

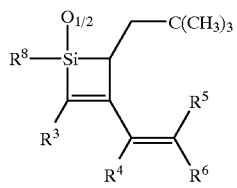

wherein $R^3$ is a monovalent hydrocarbon group free of conjugated aliphatic unsaturation or triorganosilyl; $R^5$ is hydrogen or a monovalent hydrocarbon group free of conjugated aliphatic unsaturation; $R^4$ and $R^6$ are independently hydrogen or a monovalent hydrocarbon group free of conjugated aliphatic unsaturation or together are an alkanediyl group, wherein the alkanediyl group and the carbon atoms to which it is attached form a carbocyclic ring having 4 to 7 carbon atoms; and $R^8$ is chloro, triorganosiloxy, organooxy, triorganosilyl, a monovalent hydrocarbon group, hydroxy, or —O—; provided that $R^3$ is not aryl.

20. The siloxane polymer according to claim 19, wherein the polymer is a homopolymer.

21. The siloxane polymer according to claim 19, wherein the polymer is a copolymer.

22. The siloxane polymer according to claim 19, wherein $R^3$ is triorganosilyl.

23. The siloxane polymer according to claim 22, wherein $R^3$ is trimethylsilyl.

24. The siloxane polymer according to claim 19, wherein $R^4$ and $R^6$ together are ethane-1,2-diyl, propane-1,3-diyl, or butane-1,4-diyl.

25. The siloxane polymer according to claim 19, wherein $R^4$ and at least one of $R^5$ and $R^6$ are aryl.

* * * * *